United States Patent
Itaya et al.

(10) Patent No.: US 11,202,745 B2
(45) Date of Patent: Dec. 21, 2021

(54) REDUCING COMPOSITION FOR PERMANENTLY RESHAPING KERATIN FIBERS

(71) Applicant: L'Oreal, Paris (FR)

(72) Inventors: Ayako Itaya, Kawasaki (JP); Kenichi Morita, Kawasaki (JP); Kayo Yamada, Kawasaki (JP)

(73) Assignee: L'OREAL, Paris (FR)

( * ) Notice: Subject to any disclaimer, the term of this patent is extended or adjusted under 35 U.S.C. 154(b) by 148 days.

(21) Appl. No.: 16/595,680

(22) Filed: Oct. 8, 2019

(65) Prior Publication Data

US 2020/0030207 A1 Jan. 30, 2020

Related U.S. Application Data

(62) Division of application No. 14/901,816, filed as application No. PCT/JP2014/068240 on Jul. 2, 2014, now abandoned.

(30) Foreign Application Priority Data

Jul. 3, 2013 (JP) ................................ 2013-139546

(51) Int. Cl.
| | | |
|---|---|---|
| A61K 8/46 | (2006.01) | |
| A61K 8/19 | (2006.01) | |
| A61K 8/36 | (2006.01) | |
| A61K 8/362 | (2006.01) | |
| A61K 8/41 | (2006.01) | |
| A61K 8/86 | (2006.01) | |
| A61Q 5/04 | (2006.01) | |
| A45D 2/00 | (2006.01) | |
| A45D 7/06 | (2006.01) | |

(52) U.S. Cl.
CPC ............... *A61K 8/46* (2013.01); *A45D 2/001* (2013.01); *A45D 7/06* (2013.01); *A61K 8/19* (2013.01); *A61K 8/36* (2013.01); *A61K 8/362* (2013.01); *A61K 8/41* (2013.01); *A61K 8/416* (2013.01); *A61K 8/86* (2013.01); *A61Q 5/04* (2013.01); *A61K 2800/5422* (2013.01); *A61K 2800/596* (2013.01); *A61K 2800/5922* (2013.01); *A61K 2800/805* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 4,273,143 A | 6/1981 | Klemm et al. | |
| 4,653,517 A * | 3/1987 | Inoue ..................... | A45D 2/001 |
| | | | 132/229 |
| 5,362,487 A | 11/1994 | Nandagiri et al. | |
| 5,554,363 A | 9/1996 | Nandagiri et al. | |
| 5,554,364 A | 9/1996 | Neill et al. | |
| 5,612,023 A | 3/1997 | Kiyomine et al. | |
| 6,017,519 A | 1/2000 | Rose et al. | |
| 2006/0096042 A1 | 5/2006 | Schonert et al. | |
| 2006/0260632 A1* | 11/2006 | Campain .................. | A61Q 5/04 |
| | | | 132/204 |
| 2011/0048447 A1 | 3/2011 | Mueller et al. | |

FOREIGN PATENT DOCUMENTS

| | | |
|---|---|---|
| DE | 3707415 A1 | 9/1988 |
| DE | 4317663 A1 | 12/1994 |
| EP | 0286774 A1 | 10/1988 |
| EP | 0628301 A1 | 12/1994 |
| JP | 072635 A | 1/1995 |
| JP | 2002356410 A | 12/2002 |
| WO | 2005020943 A1 | 3/2005 |
| WO | 2009063042 A1 | 5/2009 |

OTHER PUBLICATIONS

English machine translation and original German document—Maresch et al. DE 43 17 663 A1—pp. 1-18 (Year: 1994).
PCT/JP2014/068240, "International Search Report Received."
PCT/JP2014/068240, "Written Opinion Received."

* cited by examiner

*Primary Examiner* — Aradhana Sasan
(74) *Attorney, Agent, or Firm* — Buchanan Ingersoll & Rooney PC

(57) ABSTRACT

A process for permanently reshaping keratin fibers comprising mixing a component A and a component B to form a reducing composition. The component A comprises at least one thiol-based reducing compound having one thiol group selected from the group consisting of thioglycolic acid and derivatives thereof, thiolactic acid and derivatives thereof, 3-mercaptopropionic acid and derivatives thereof, and cysteine and derivatives thereof, and has pH 7.0 or less and the component B comprises at least one buffer salt selected from the group consisting of carbonates, bicarbonates and carbamates, and has pH 8.0 or more, wherein at least one of the component A and component B comprises at least one disulfide compound that is further defined, and wherein the reducing composition has a pH ranging from 7.0 to 7.8 and a viscosity ranging from 500 cps to 100,000 cps. The reducing composition is then applied to the keratin fibers.

19 Claims, No Drawings

REDUCING COMPOSITION FOR PERMANENTLY RESHAPING KERATIN FIBERS

CROSS-REFERENCE TO RELATED APPLICATIONS

This application is a divisional of U.S. application Ser. No. 14/901,816, filed Dec. 29, 2015, now abandoned, which is a U.S. national stage application of PCT/JP2014/068240, filed Jul. 2, 2014, which claims priority to Japanese Patent Application No. 2013-139546, filed Jul. 3, 2013, the contents of all of which are hereby incorporated by reference.

TECHNICAL FIELD

The present invention relates to a reducing composition for permanently reshaping keratin fibers, preferably having substantially neutral pH. The present invention also relates to a process for permanently reshaping keratin fibers under heat environment using said reducing composition.

BACKGROUND ART

Useful art to obtain a permanent reshaping or deforming process of keratin fibers such as hair may be, in a first step, in opening the keratin disulfide bonds (cystine) with a composition comprising a reducing agent, and preferably after rinsing the keratin fibers, in reforming, in a second step, said disulfide bonds by applying to the keratin fibers which have been placed beforehand under mechanical tension with curlers or equivalents thereof or which have been straightened by other means, an oxidizing composition, so as to give the desired form to the keratin fibers. This process enables either the waving of the keratin fibers or the decurling, the backcombing or the straightening thereof. However, this may not lead to sufficient waving/straightening effects.

Recently, a new permanent process in which a heating step is added after rinsing of reducing agent in the above-mentioned process is popular, in particular, in Asian countries. This new process also enables either the waving of the keratin fibers or the decurling, the backcombing or the straightening thereof. Also, this new process, can lead to sufficient waving/straightening effects such as good wave/straightening performance and their good durability.

However, in the processes for permanently reshaping keratin fibers, a composition comprising a reducing agent is normally used at a pH ranging from 8 to 10, which can lead to hair damage. Further, a composition comprising a reducing agent is usually in the form of liquid because the application is done after winding of hair on rods. But in case of this new process since the application is done without winding, once applied onto keratin fibers, drippings of such composition are running down the forehead, the nape, and the face or is getting into the eyes, thus such drippings give an uncomfortable feeling and/or a safety issue. In addition, it is necessary to improve retention time of the reducing composition onto keratin fibers, in particular, under heat environment, so as to give sufficient waving effects such as good wave/straightening performance and their good durability.

As for the former drawback, it has already been tried to overcome it by the development of so-called "acidic permanent waving compositions" having a pH ranging from about 6.8 to 7.8, which is close to neutral. However, some ingredients in a conventional composition comprising a reducing agent are not stable at acidic and neutral pH, thus the effect of those compositions were not optimal.

In view of such faults, for example JP 1995-2635 A and U.S. Pat. No. 6,017,519 disclose a reducing composition prepared by mixing two components at the time of use, one component comprising a reducing agent and having acidic pH, and another component comprising an unstable substance at acidic and neutral pH and having basic pH, respectively.

SUMMARY OF INVENTION

Problems to be Solved by the Invention

Therefore, there is a need for providing a reducing composition which solves the problems of the prior art. In particular, there is a need for providing a reducing composition which gives sufficient waving effects, has substantially neutral pH and with no problem of stability, and advantageously has an appropriate viscosity sufficient not to induce drippings.

Means to Solve the Problems

The inventors have found a reducing composition with substantially neutral pH for permanently reshaping keratin fibers such as hair, prepared by mixing two components at the time of use. The reducing composition of the present invention has a pH about neutrality and does not involve a problem of stability.

Thus, in one aspect of the present invention, there is provided a reducing composition for permanently reshaping keratin fibers such as hair, prepared by mixing a component A and a component B at the time of use, wherein
- the component A comprises at least one thiol-based reducing compound and has pH 7.0 or less,
- the component B comprises at least one buffer salt selected from the group consisting of carbonates, bicarbonates and carbamates, and has pH 8.0 or more,
- at least one of the component A and component B comprises at least one disulfide compound, and
- the reducing composition prepared has pH ranging from 7.0 to 7.8.

It is preferable that the composition has a viscosity ranging from 500 cps to 100,000 cps, and more preferably ranging from 2,000 cps to 50,000 cps.

According to the present invention, at least one of the component A and the component B may further comprise at least one surfactant, wherein the surfactant may be selected from the group consisting of cationic, anionic, nonionic and amphoteric surfactants, and preferably is a cationic surfactant. Here, the cationic surfactant may be selected from the group consisting of alkyltrimethylammonium salts, preferably behentrimonium chloride, and the nonionic surfactant may be selected from the group consisting of polyoxyethylene alkyl ethers, preferably polyoxyethylated cetyl and stearyl alcohols and their mixtures.

According to the present invention, the component A may have pH ranging from 3.5 to 6.5, and the component B has pH ranging from 8.0 to 9.0.

According to the present invention, the buffer salt may be at least one selected from the group consisting of bicarbonates, preferably ammonium bicarbonate.

According to the present invention, the thiol-based reducing compound may be selected from the group consisting of thioglycolic acid and derivatives thereof; dithioglycolic acid and derivatives thereof; thiolactic acid and derivatives thereof; 3-mercaptopropionic acid and derivatives thereof; cysteamine and derivatives thereof; mono-thioglycerol and derivatives thereof; and cysteine and derivatives thereof. Preferred is that the thiol-based reducing compound may be selected from the group consisting of thioglycolic acid and salts thereof; and thiolactic acid and salts thereof.

According to the present invention, the disulfide compound may be a disulfide of the thiol-based reducing compound used, preferably is selected from dithiodiglycolates.

According to the present invention, at least one of the component A and the component B further may comprise at least one sequestering agent, preferably pentasodium pentetate; a pH regulator.

According to the present invention, the component A may be in the form of liquid, emulsion or gel, and the component B may be in the form of liquid, emulsion or gel.

Further, in another aspect of the present invention, there is provided a kit for permanently reshaping keratin fibers such as hair, comprising:
 a component A comprising at least one thiol-based reducing compound and having pH 7.0 or less;
 a component B comprising at least one buffer salt selected from the group consisting of carbonates, bicarbonates and carbamates, and having pH 8.0 or more;
 wherein at least one of the component A and component B comprises at least one disulfide compound, and the component A and component B are mixed to prepare a reducing composition having pH ranging from 7.0 to 7.8, and optionally further comprising:
 an oxidizing composition comprising at least one oxidizing compound.

The reducing composition according to the present invention is intended for permanently reshaping keratin fibers such as hair under heat environment.

Furthermore, in another aspect of the present invention, there is provided a process for permanently reshaping keratin fibers such as hair using the reducing composition as defined above and comprising at least one step of heating.

Preferably this process comprises the following steps of:
(i) applying onto the keratin fibers the reducing composition as described hereinbefore;
(ii) rinsing said keratin fibers with water and optionally drying the keratin fibers;
(iii) setting said keratin fibers under mechanical tension;
(iv) heating said keratin fibers, preferably at a temperature ranging from 60 to 250° C.; and
(v) applying onto said keratin fibers an oxidizing composition comprising at least one oxidizing compound.

It is preferable that the process comprises a step of moistening the keratin fibers before the application step (i); and/or a step of leaving the keratin fibers for 10 to 30 minutes after the application step (i) and before the rinsing step (ii); and/or a step of leaving the keratin fibers for 5 to 15 minutes after the application step (v); and/or a step of rinsing said keratin fibers with water and optionally drying said keratin fibers after the application step (v).

According to the present invention, the step (iii) may be a step of winding said keratin fibers on a rod, or a step of straightening said keratin fibers with an iron.

It is also preferable that the oxidizing compound be at least one selected from the group consisting of hydrogen peroxide, alkaline bromate, polythionates and persalts, more preferably hydrogen peroxide.

Effects of the Invention

The reducing composition of the present invention can solve the problems of the prior art. That is, the reducing composition gives sufficient waving effects such as good wave/straightening performance and their good durability, has neutral pH and avoids problem of stability, and advantageously may have an appropriate viscosity sufficient not to induce drippings.

EMBODIMENTS TO CARRY OUT THE INVENTION

Reducing Composition

The reducing composition of the present invention comprises of a component A and a component B. Here, the component A comprises at least one thiol-based reducing compound and has pH 7.0 or less, and the component B comprises at least one buffer salt selected from the group consisting of carbonates, bicarbonates and carbamates, and has pH 8.0 or more. In addition, at least one of the component A and the component B comprises a disulfide compound. The reducing composition of the present invention is prepared by mixing the component A and the component B at the time of use, and then the reducing composition prepared has neutral pH ranging from 7.0 to 7.8.

Ingredients in Component A

Thiol-Based Reducing Compound

The component A of the present invention comprises at least one thiol-based reducing compound, preferably one, two, three or four thiol-based reducing compounds.

As used herein, the "thiol-based reducing compound" means a compound having one or more thiol (—SH) groups, said thiol group(s) being optionally in the form of an organic or inorganic salt.

The thiol-based reducing compound may preferably be selected from the group consisting of thioglycolic acid and derivatives thereof, in particular esters thereof such as glycerol or glycol monothioglycolate; dithioglycolic acid and derivatives thereof, in particular esters thereof such as glycerol or glycol dithioglycolate; thiolactic acid and derivatives thereof, in particular esters thereof such as glycerol monothiolactate; 3-mercaptopropionic acid and derivatives thereof, in particular esters thereof such as glycerol 3-mercaptopropionate and ethyleneglycol 3-mercaptopropionate; cysteamine and derivatives thereof, in particular $C_{1-4}$ acyl derivatives thereof such as N-acetylcysteamine and N-propionylcysteamine; mono-thioglycerol and derivatives thereof, in particular esters; and cysteine and derivatives thereof, in particular $C_{1-4}$ acyl derivatives thereof such as N-acetylcysteine, N-alkanoylcysteine and esters thereof such as cysteine alkyl esters. The derivatives mentioned in the above may include salts thereof.

As the above salts, mention may be made of, for example, ammonium salts; primary-, secondary- or tertiary-amine salts; alkaline metal salts; and alkaline earth metal salts. As the primary-, secondary- or tertiary-amine, for example, monoethanolamine, di-isopropanolamine or triethanolamine may be mentioned respectively.

The thiol-based reducing compound may more preferably be selected from the group consisting of thioglycolic acid and salts thereof; and thiolactic acid and salts thereof, most preferably be selected from the group consisting of thioglycolic acid, thiolactic acid and ammonium salts thereof.

The thiol-based reducing compound(s) may be used in sufficient amounts to reduce the keratin fiber disulfide bonds. Generally, the amount of the thiol-based reducing compound(s) can be from 0.1 to 20%, preferably from 1 to 15% by weight of the total weight of the reducing composition.

pH Value

The component A of the present invention has pH 7.0 or less, preferably pH ranging from 3.5 to 6.5. The pH value of the component A may be adjusted by the combination of two or more thiol-based reducing compounds or by adding a pH regulator. The pH regulator may be cosmetically acceptable and preferably be selected from organic or inorganic acids and organic or inorganic alkalines, as referred to hereinafter.

Properties

The component A of the present invention may be in the form of liquid, gel or emulsion, preferably liquid or gel. Depending on the desired form, kinds and amounts of medium (as referred to hereinafter) may be used appropriately, and if necessary, any additional ingredients such as surfactants (as referred to hereinafter) or thickeners (as referred to hereinafter) may be added. In case of any forms, the component A may have an appropriate viscosity which can provide a given viscosity for the reducing composition of the present invention in mixing it with the component B.

Ingredients in Component B

Buffer Salt

The component B of the present invention comprises at least one buffer salt which can keep the pH value of the component B alkaline (pH 8 or more). The buffer salt is selected from the group consisting of carbonates, bicarbonates and carbamates, preferably selected from the group consisting of alkaline metals, alkaline earth metals and ammonium salts of carbonate, bicarbonate and carbamate. In particular, preferred buffer salt is sodium carbonate, ammonium carbonate, sodium bicarbonate, ammonium bicarbonate and sodium carbamate or ammonium carbamate.

Here, the buffer salt(s) may be used in sufficient amounts to keep the pH value of the component B alkaline (pH 8 or more). Typically, the amount of the buffer salt(s) can be from 0.5 to 15%, preferably from 1 to 10%, and more preferably from 2 to 8% by weight of the total weight of the reducing composition.

pH Value

The component B of the present invention has pH 8.0 or more, preferably pH ranging from 8.0 to 9.0. The pH value of the component B may be adjusted by only a selection of the buffer salt(s) or by further adding a pH regulator. The pH regulator may be cosmetically acceptable and preferably be selected from organic or inorganic acids and organic or inorganic alkalines other than carbonates, bicarbonates and carbamates, as referred to hereinafter.

Properties

The component B of the present invention may be in the form of liquid, gel or emulsion, preferably gel or emulsion. Depending on the desired form, kinds and amounts of medium (as referred to hereinafter) may be used appropriately, and if necessary, any additional ingredients such as surfactants (mentioned hereinafter) or thickeners (mentioned hereinafter) may be added. In case of any forms, the component B may have an appropriate viscosity which can provide a prescribed viscosity for the reducing composition of the present invention in mixing it with the component A.

Ingredients in the Component A and/or the Component B

Disulfide Compound

At least one of the component A and the component B comprises one or more disulfide compounds. These compounds act as reaction regulators. Generally the reaction regulator is added to control a reaction rate between the thiol-based reducing compound and the keratin fiber disulfide bonds in view of equilibrium in the reaction, thereby inhibiting excessive reaction progress. Thus, the disulfide compound as a reaction regulator may be a disulfide issued from the thiol-based reducing compound as mentioned above, and having —S—S— bond, such as dithioglycolic acid and salts thereof dithiodilactic acid and salts thereof cystamine and salts thereof and cystine and salts thereof. As the above salts, mention may be made of, for example, ammonium salts; primary-, secondary- or tertiary-amine salts; alkaline metal salts; and alkaline earth metal salts. The disulfide compound as a reaction regulator may be preferably dithioglycolic acid and salts thereof such as ammonium dithioglycolate; dithiodilactic acid and salts thereof; cystamine and salts thereof; and cystine and salts thereof.

Here, the wording "at least one of the component A and component B" means either the component A or component B, or both of the component A and component B. Thus, either the component A or component B may comprise the disulfide compound(s), or both may comprise the disulfide compound(s) respectively. Preferred is that the component A comprises the disulfide compound(s).

The disulfide compound may be used in amounts to control the reaction rate appropriately. Typically, the amount of the disulfide compound(s) can be from 0.1 to 10%, preferably from 2 to 5% by weight of the total weight of the reducing composition.

Optional Ingredients in the Component A and/or the Component B

Surfactant

At least one of the component A and the component B may comprise one or more surfactants to homogenize the ingredients in the component A and/or the component B or to make the component A and/or the component B the desired form such as liquid, gel or emulsion. The surfactant can be selected from cationic, anionic, nonionic and amphoteric surfactants, preferably cationic and/or nonionic surfactants, more preferably cationic surfactants.

Examples of the cationic surfactant include $C_{6-30}$ alkyl amine salts such as cocoalkylamine acetate and stearylamine acetate; and quaternary ammonium salts, in particular $C_{6-30}$ alkyltrimethylammonium salts such as behentrimonium chloride (docosyl trimethyl ammonium chloride), cocoalkyl trimethyl ammonium chloride, stearyl trimethyl ammonium chloride and cetyl trimethyl ammonium chloride. Preferred examples of the cationic surfactant include quaternary ammonium salts, in particular $C_{6-30}$ alkyltrimethylammonium salts such as behentrimonium chloride (docosyl trimethyl ammonium chloride), cocoalkyl trimethyl ammonium chloride, stearyl trimethyl ammonium chloride and cetyl trimethyl ammonium chloride.

Examples of the anionic surfactant include $C_{6-30}$ alkyl sulfates and salts thereof such as sodium lauryl sulfate, ammonium lauryl sulfate and triethanolamine lauryl sulfate; polyoxyethylene $C_{6-30}$ alkyl ether sulfates and salts thereof such as ammonium polyoxyethylene lauryl ether sulfate and sodium polyoxyethylene lauryl ether sulfate; $C_{6-30}$ alkyl benzene sulfonates and salts thereof such as sodium dodecyl benzene sulfonate; $C_{6-30}$ alkyl benzene sulfonic acids such as dodecyl benzene sulfonic acid; other sulfonates such as sodium alkyl naphthalene sulfonates, sodium dialkyl sulfosuccinates and sodium alkyl diphenyl ether disulfonates; $C_{6-30}$ fatty acid salts such as sodium stearate and potassium oleate; and polyoxyethylene $C_{6-30}$ alkyl ether carboxylic acid such as polyoxyethylene lauryl ether carboxylic acid.

Examples of the nonionic surfactant include polyoxyethylene $C_{6-30}$ alkyl ethers such as polyoxyethylene lauryl ether, polyoxyethylene octyldodecyl ether, polyoxyethylene cetyl ether, polyoxyethylene stearyl ether, polyoxyethylene myristyl ether and a mixture thereof; these ethers are polyoxyethylated fatty alcohols; sorbitan $C_{6-30}$ fatty acid esters such as sorbitan monolaurate, sorbitan monopalmitate, sorbitan monostearate, sorbitan tristearate, sorbitan monooleate, sorbitan trioleate and a mixture thereof; polyoxyethylene sorbitan $C_{6-30}$ fatty acid esters such as polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate and polyoxyethylene sorbitan trioleate; glycerol $C_{6-30}$ fatty acid esters such as glycerol monostearate and glycerol monooleate; polyoxyethylene hydrogenated caster oils; and $C_{6-30}$ fatty acid alkanolamides such as coconut monoethanolamide and coconut diethanolamide. Preferred examples of the nonionic surfactant include polyoxyethylene $C_{6-30}$ alkyl ethers such as polyoxyethylene cetyl ether or polyoxyethylated cetyl alcohol (the INCI name: CETETH-n, wherein n is a number of oxyethylene unit), polyoxyethylene stearyl ether or polyoxyethylated stearyl alcohol, and a mixture thereof (the INCI name: CETEARETH-n, wherein n is a number of oxyethylene unit).

Examples of the amphoteric surfactant include betaines such as lauramidopropyl betaine, lauryl betaine, cocamide propyl betaine, stearyl betaine and dimethyllaurylaminoacetate betaine; and non betainic amphoteric surfactants such as cocoamphodiacetate.

Either the component A or component B may comprise the surfactant(s), or both may comprise the surfactant(s) respectively. Preferred is that the component B comprises the surfactant(s).

Typically, the amount of the surfactant(s) can be from 0.01 to 10% by weight, preferably from 0.05 to 5% by weight and more preferably from 0.1% to 3.0% by weight of the total weight of the reducing composition.

Sequestering Agent

At least one of the component A and the component B may comprise one or more sequestering agents. The sequestering agent can be cosmetically acceptable and commercially available. Examples of the sequestering agent include ethylene diamine tetraacetic acid (EDTA), N-(hydroxyethyl) ethylene diamine triacetic acid, aminotrimethylene phosphonic acid, diethylenetriamine-pentaacetic acid (i.e., pentetic acid), lauroyl ethylene diamine triacetic acid, nitrilotriacetic acid, iminodisuccinic acid, tartaric acid, citric acid, N-2-hydroxyethyliminodiacetic acid and salts thereof. Preferred examples of the sequestering agents include ethylene diamine tetraacetic acid (EDTA) or salts thereof such as tetrasodium ethylene diamine tetraacetate; and diethylenetriamine-pentaacetic acid or salts thereof such as pentasodium diethylenetriamine-pentaacetate (i.e., pentasodium pentetate).

Either the component A or component B may comprise the sequestering agent(s), or both may comprise the sequestering agent(s) respectively. Preferred is that both comprises the sequestering agent(s).

Typically, the amount of the sequestering agent(s) can be from 0.001 to 2.0% by weight, preferably from 0.05 to 1.0% by weight and more preferably from 0.1% to 0.5% by weight of the total weight of the reducing composition.

pH Regulator

At least one of the component A and the component B may comprise one or more pH regulators, the pH regulator being other than carbonates, bicarbonates and carbamates for component B. The pH regulator may be selected from cosmetically acceptable organic or inorganic acids and organic or inorganic alkalines. Typically, examples of organic or inorganic acids include hydrochloric acid, citric acid, phosphoric acid and salts thereof. Further, examples of organic or inorganic alkalines include ammonia; amino alcohols such as monoethanol amine, triethanol amine, isopropanol amine, 2-amino-2-methyl-1-propanol and 2-amino-2-methyl-1,3-propanediol; basic amino acids such as L-arginine; morpholine; phosphates such as sodium phosphate dibasic and ammonium phosphate dibasic; and caustic alkalines such as potassium hydroxide and sodium hydroxide.

Either the component A or component B may comprise the pH regulator(s), or both may comprise the pH regulator(s) respectively.

Medium

Components A and B may comprise water such as pure water, ultrapure water, demineralized water and deionized water. They may also comprise organic solvents such as lower alcohols such as alcohols with $C_{1-5}$ alkyl, in particular, ethanol, propanol, isopropanol and butanol; polyols such as glycerol, ethylene glycol, propylene glycol, polyethylene glycol and sorbitol; and polyol monoalkyl ethers such as ethylene glycol monoethyl ether, ethylene glycol monobutyl ether, propylene glycol monoethyl ether, propylene glycol monobutyl ether, diethylene glycol monoethyl ether and diethylene glycol monobutyl ether.

Preferably components A and B comprise water.

Other Adjuvants

The component A and the component B to prepare the reducing composition as disclosed herein may also comprise at least one adjuvant selected, for example, from silicones in soluble, dispersed and microdispersed forms; ceramides, glycoceramides and pseudoceramides; vitamins and provitamins including panthenol; waxes other than ceramides, glycoceramides and pseudoceramides; water-soluble and liposoluble, silicone-based and non-silicone-based sunscreens; nacreous agents and opacifiers; plasticizers; solubilizers; thickeners such as carboxymethyl cellulose, carboxyvinyl polymer, and (meth)acrylate copolymers/homopolymers as described in WO 2009/063042 A1; antioxidants; penetrating agents; fragrances; preserving agents; viscosity modifiers such as higher alcohols, for example, cetanol and mineral oil; humectant; hair protective agents such as amino acids, polypeptides and polymers.

Preparation of the Reducing Composition

The reducing composition of the present invention is prepared by mixing the component A and the component B at the time of use. The resulting reducing composition has neutral pH, ranging from 7.0 to 7.8 and preferably has a viscosity ranging from 500 cps to 100,000 cps, more preferably ranging from 2,000 cps to 50,000 cps, more preferably ranging from 5,000 cps to 25,000 cps, and most preferably ranging from 5,000 cps to 10,000 cps, measured with a Brookfield viscometer at 25° C. In case the viscosity of the reducing composition is 500 cps or more, drippings of the reducing composition which give a subject an uncomfortable feeling can be reduced or suppressed. In addition, in case the viscosity of the reducing composition is 100,000 cps or less, it may be easier for a user (a practitioner, a hairdresser or the like) to mix the component A and the component B at the time of use to prepare the reducing composition on site and it is easy to apply it onto hair. The reducing composition of the present invention thus obtained is intended for permanently reshaping keratin fibers such as hair, in particular, under heat environment.

Kit for Permanently Reshaping Keratin Fibers

A kit of the present invention comprises a component A, a component B and optionally an oxidizing composition. Here, the component A and the component B are the same as those as mentioned above. Typically, the component A and the component B will be mixed with each other at the time of use to prepare the reducing composition of the present invention as mentioned above by a practitioner (for example, a hairdresser or the like) on site. This preparation shall result in the reducing composition with substantially neutral pH (pH 7.0 to 7.8). Thus a kit of the present invention is preferably single-use type comprising a single dose of the component A and a single dose of the component B.

A kit of the present invention may comprise the oxidizing composition. The oxidizing composition comprises at least one oxidizing compound. The oxidizing compound can be selected from cosmetically acceptable, conventional oxidizers, for example, at least one selected from the group consisting of hydrogen peroxide; alkaline bromate such as potassium bromate and sodium bromate; polythionates; and persalts such as sodium perborate; preferably the oxidizer is hydrogen peroxide.

Process for Permanently Reshaping Keratin Fibers

The reducing composition of the present invention can be used in a process for permanently reshaping keratin fibers such as hair, preferably with a step of heating, typically comprising the following steps of: (i) applying onto the keratin fibers the reducing composition of the present invention prepared at the time of use; (ii) rinsing said keratin fibers with water and optionally drying the keratin fibers; (iii) setting said keratin fibers under mechanical tension; (iv) heating said keratin fibers, preferably under a temperature ranging from 60 to 250° C.; and (v) applying onto said keratin fibers an oxidizing composition comprising at least one oxidizing compound, preferably as mentioned above.

The process may further comprise the following steps of: moistening the keratin fibers before the application step (i); leaving the keratin fibers for 10 to 30 minutes after the application step (i) and before the rinsing step (ii); leaving the keratin fibers for 5 to 15 minutes after the application step (v); rinsing said keratin fibers with water and optionally drying said keratin fibers after the application step (v).

In the step (iii), the mechanical tension may be provided by at least one reshaping means selected from the group consisting of a curler, a roller, a rod, a plate and an iron. Thus, the step (iii) may be a step of winding said keratin fibers on a rod, or a step of straightening said keratin fibers with an iron.

EXAMPLES

The present invention will be described in more detail by way of examples, which however should not be construed as limiting the scope of the present invention.

Preparation 1: Preparation for Component A

Component A1 was prepared according to the formulation shown in Table 1. The resulting component A was liquid and pH value thereof was 5.0.

TABLE 1

| Component A1 | |
|---|---|
| Ingredients | wt % |
| Pentasodium pentetate (40% in aq. Solution) | 0.4 |
| Thioglycolic acid | 10.2 |
| Ammonium thioglycolate (71% in aq. Solution) | 53 |
| Ammonium thiolactate (58% in aq. Solution) | 12 |
| Water | qs to 100 |

Preparations 2 to 4: Preparations for Component B

Components B1 to B3 were prepared according to the formulations shown in Table 2. The resulting components B1 to B3 were emulsions.

TABLE 2

| Ingredients | Component B1 wt % | Component B2 wt % | Component B3 wt % |
|---|---|---|---|
| Behentrimonium Chloride | 3 | 3 | 3 |
| Ceteareth-25 | 2 | 2 | 2 |
| Ceteth-2 | 1 | 1 | 1 |
| Cetanol | 3 | 3 | 3 |
| Mineral oil | 2 | 2 | 2 |
| Pentasodium pentetate (40% in aq. Solution) | 0.4 | 0.4 | 0.4 |
| Ammonium bicarbonate | 4 | 8 | — |
| Diammonium dithiodiglycolate (48% in aq. Solution) | 7.3 | 7.3 | 7.3 |
| Ethanolamine | pH adjust (pH 8) | pH adjust (pH 8) | pH adjust (pH 8) |
| Water | qs to 100 | qs to 100 | qs to 100 |

Preparation 5: Preparations for Control

As control, a conventional reducing composition with alkaline pH was prepared according to the formulation shown in Table 3. The resulting control was liquid and pH value thereof was 9.

TABLE 3

| Control | |
|---|---|
| Ingredients | wt % |
| Pentasodium pentetate (40% in aq. Solution) | 0.4 |
| Ammonium thioglycolate (71% in aq. Solution) | 15 |
| Behentrimonium Chloride | 2.3 |
| Ceteareth-25 | 1.4 |
| Ceteth-2 | 0.8 |
| Cetanol | 2.1 |
| Mineral oil | 1.2 |
| Diammonium dithiodiglycolate (48% in aq. Solution) | 5 |
| Ethanolamine | 1.2 |
| Ammonium hydroxide (20% in aq. Solution) | 2 |
| Water | qs to 100 |

Example 1

Component A1 and component B1 obtained in Preparations 1 and 2 respectively were mixed in a weight ratio of 1:3 at the time of being subjected to the following evaluation method. Results of the evaluations have been shown in Table 4.

<Evaluation Method for Digital Perm>

Hair was moistened and then the reducing composition of Example 1 was applied to the hair. The hair was left for 15 minutes and then rinsed thoroughly with water. The hair was winded on a rod for a digital perm and then heated for 25 minutes at temperature 90° C. An oxidizing composition comprising hydrogen peroxide was applied to the hair and left for 5 minutes, and then the hair was rinsed thoroughly with water and dried.

The hair which had been treated as above was evaluated sensorially by experts on the evaluation points "Wave intensity", "Wave bounciness", "Smoothness" and "Suppleness".

Example 2

Component A1 and component B2 obtained in Preparations 1 and 3 respectively were mixed in a weight ratio of 1:3 at the time of being subjected to the above evaluation method for digital perm. Results of the evaluations have been shown in Table 4.

Comparative Example 1

Component A1 and component B3 obtained in Preparations 1 and 4 respectively were mixed in a weight ratio of 1:3 at the time of being subjected to the above evaluation method for digital perm. Results of the evaluations have been shown in Table 4.

Comparative Example 2

Control obtained in Preparation 5 was subjected to the above evaluation method for digital perm. Results of the evaluations have been shown in Table 4.

TABLE 4

|  | Reducing composition (mixing ratio) | pH | viscosity (cps) | Wave intensity | Wave bounciness | Smoothness | Suppleness |
|---|---|---|---|---|---|---|---|
| Example 1 | A1 + B1 (1:3) | 7 | 8,000-8,500 | ± | ± | + | + |
| Example 2 | A1 + B2 (1:3) | 7 | 8,000-8,500 | + | + | + | + |
| Comparative Example 1 | A1 + B3 (1:3) | 7 | 8,000-8,500 | − | − | + | + |
| Comparative Example 2 | Control | 9 | 10,000-10,500 | + | ± | ± | − |

Evaluation criteria shown in the symbols "+", "±" and "−" on each evaluation point in Table 4 have the following meanings.

Wave intensity: +: better wave efficiency; ±: Neither; −: less wave efficiency

Wave bounciness: +:better bounciness; ±: Neither; −: less bounciness

Smoothness: +:better smoothness; ±: Neither; −: less smoothness

Suppleness: +:better suppleness; ±: Neither; −: less suppleness

Example 3

Component A1 and component B1 obtained in Preparations 1 and 2 respectively were mixed in a weight ratio of 1:3 at the time of being subjected to the following evaluation method. Results of the evaluations have been shown in Table 5.

<Evaluation Method for Iron Straightener>

Hair was moistened and then the reducing composition of Example 3 was applied to the hair. The hair was left for 15 minutes and then rinsed thoroughly with water. The hair was dried about 80% using a dryer and then ironed at temperature 180° C. The hair was parted into 4 sections. Next, the hair was gently combed through parting. Then the hair was ironed approximately ⅛ inch from scalp. Each parting was ironed 2 to 3 times. This process was repeated until all hair has been ironed. An oxidizing composition comprising hydrogen peroxide was applied to the hair and left for 5 minutes, and then the hair was rinsed thoroughly with water and dried.

The hair which had been treated as above was evaluated sensorially by experts on the evaluation points "Straightening effect", "Volume down", "Smoothness" and "Suppleness".

Example 4

Component A1 and component B2 obtained in Preparations 1 and 3 respectively were mixed in a weight ratio of 1:3 at the time of being subjected to the above evaluation method for iron straightener. Results of the evaluations have been shown in Table 5.

Comparative Example 3

Component A1 and component B3 obtained in Preparations 1 and 4 respectively were mixed in a weight ratio of 1:3 at the time of being subjected to the above evaluation method for iron straightener. Results of the evaluations have been shown in Table 5.

Comparative Example 4

Control obtained in Preparation 5 was subjected to the above evaluation method for iron straightener. Results of the evaluations have been shown in Table 5.

TABLE 5

|  | Reducing composition (mixing ratio) | pH | viscosity (cps) | Straightening effect | Volume down | Smoothness | Suppleness |
|---|---|---|---|---|---|---|---|
| Example 3 | A1 + B1 (1:3) | 7 | 8,000-8,500 | ± | ± | + | + |
| Example 4 | A1 + B2 (1:3) | 7 | 8,000-8,500 | + | + | + | + |
| Comparative Example 3 | A1 + B3 (1:3) | 7 | 8,000-8,500 | − | − | + | + |
| Comparative Example 4 | Control | 9 | 10,000-10,500 | + | + | ± | − |

Evaluation criteria shown in the symbols "+", "±" and "−" on each evaluation point in Table 5 have the same meanings as defined in Table 4.

The invention claimed is:

1. A process for permanently reshaping keratin fibers comprising:

mixing a component A and a component B to form a reducing composition, wherein the component A comprises at least one thiol-based reducing compound having one thiol group selected from the group consisting of thioglycolic acid and derivatives thereof, thiolactic acid and derivatives thereof, 3-mercaptopropionic acid and derivatives thereof, and cysteine and derivatives thereof, and has pH 7.0 or less, the component B comprises at least one buffer salt selected from the group consisting of carbonates, bicarbonates and carbamates, and has pH 8.0 or more, wherein at least one of the component A and component B comprises at least one disulfide compound which is a separate compound that corresponds to the thiol-based reducing compound having one thiol group, and wherein the reducing composition has a pH ranging from 7.0 to 7.8 and a viscosity ranging from 500 cps to 100,000 cps; and applying the reducing composition to the keratin fibers.

2. The process according to claim 1, wherein the reducing composition further comprises at least one surfactant selected from the group consisting of cationic, anionic, nonionic and amphoteric surfactants.

3. The process according to claim 2, wherein the surfactant is a cationic surfactant selected from the group consisting of alkyltrimethylammonium salts.

4. The process according to claim 2, wherein the surfactant is a nonionic surfactant selected from the group consisting of polyoxyethylene alkyl fatty ethers.

5. The process according to claim 1, wherein the component A has pH ranging from 3.5 to 6.5.

6. The process according to claim 1, wherein the component B has pH ranging from 8.0 to 9.0.

7. The process according to claim 1, wherein the buffer salt is selected from the group consisting of bicarbonates.

8. The process according to claim 1, wherein the disulfide compound is a dithiodiglycolate.

9. The process according to claim 1, wherein at least one of the component A and the component B further comprises at least one sequestering agent and/or at least one pH regulator, the pH regulator being other than carbonates, bicarbonates and carbamates for component B.

10. The process according to claim 1, further comprising at least one step of heating the keratin fibers after the applying.

11. The process according to claim 10, further comprising the following steps after applying the reducing composition to the keratin fibers:

(i) rinsing said keratin fibers with water and optionally drying the keratin fibers;
(ii) setting said keratin fibers under mechanical tension;
(iii) heating said keratin fibers; and
(iv) applying onto said keratin fibers an oxidizing composition comprising at least one oxidizing compound.

12. The process according to claim 11, further comprising a step of moistening the keratin fibers before applying the reducing composition.

13. The process according to claim 11, further comprising a step of leaving the keratin fibers for 10 to 30 minutes after applying the reducing composition and before the rinsing step.

14. The process according to claim 11, further comprising a step of leaving the keratin fibers for 5 to 15 minutes after applying the oxidizing compound, followed by a step of rinsing said keratin fibers with water and optionally drying said keratin fibers.

15. The process according to claim 11, wherein the step (ii) is a step of winding said keratin fibers on a rod.

16. The process according to claim 11, wherein the step (ii) is a step of straightening said keratin fibers with an iron.

17. The process according to claim 11, wherein the oxidizing compound is at least one selected from the group consisting of hydrogen peroxide, alkaline bromate, polythionates and persalts.

18. The process according to claim 11, wherein the heating of the keratin fibers is at a temperature ranging from 60 to 250° C.

19. The process according to claim 1, wherein the keratin fibers are hair.

* * * * *